(12) United States Patent
Milo

(10) Patent No.: US 6,953,438 B2
(45) Date of Patent: Oct. 11, 2005

(54) ULTRASONIC MEDICAL DEVICE

(75) Inventor: Simcha Milo, Haifa (IL)

(73) Assignee: Neurosonix, Ltd., Or-Yehuda (IL)

(*) Notice: Subject to any disclaimer, the term of this patent is extended or adjusted under 35 U.S.C. 154(b) by 364 days.

(21) Appl. No.: 10/162,824

(22) Filed: Jun. 4, 2002

(65) Prior Publication Data

US 2003/0221561 A1 Dec. 4, 2003

Related U.S. Application Data

(63) Continuation of application No. PCT/IB00/01785, filed on Dec. 4, 2000.
(60) Provisional application No. 60/190,839, filed on Mar. 20, 2000, and provisional application No. 60/169,226, filed on Dec. 6, 1999.

(51) Int. Cl.⁷ .............................................. A61N 7/00
(52) U.S. Cl. ........................................................ 601/2
(58) Field of Search .................. 601/2–4; 600/438–439, 600/459; 623/1.6, 2.1, 2.22, 2.41

(56) References Cited

U.S. PATENT DOCUMENTS

| | | | |
|---|---|---|---|
| 3,951,136 A | 4/1976 | Wall | 128/2.06 E |
| 4,722,347 A | 2/1988 | Abrams et al. | 128/663 |
| 4,757,821 A | 7/1988 | Snyder | 128/660 |
| 4,886,059 A | 12/1989 | Weber | 128/207.15 |
| 5,022,899 A | 6/1991 | Hohlfeld et al. | 55/277 |
| 5,334,136 A | 8/1994 | Schwarz et al. | 604/4 |
| 5,811,658 A | 9/1998 | Van Driel et al. | 73/19.02 |
| 5,879,314 A | 3/1999 | Peterson et al. | 601/2 |
| 6,123,717 A | 9/2000 | Davis et al. | 607/109 |
| 6,126,619 A | 10/2000 | Peterson et al. | 601/2 |
| 6,258,120 B1 | 7/2001 | McKenzie et al. | 623/1.36 |
| 6,348,063 B1 | 2/2002 | Yassour et al. | 606/200 |
| 6,398,734 B1 * | 6/2002 | Cimochowski et al. | 600/454 |
| 6,527,718 B1 * | 3/2003 | Connor et al. | 600/439 |

OTHER PUBLICATIONS

Schwartz et al., "The Acoustic Filter: An Ultrasonic Blood Filter for the Heart–Lung Machine", J. of Thoracic and Cardiovascular Surg. (1992), pp. 1647–1653.

I.C. Macedo and Wen–Jei Yang, "Acoustic Effects on the Gas Bubbles in the Flows of Viscous Fluids and Whole Blood", J. of the Accoustical Soc. of Am. (1991), pp. 1327–1335.

* cited by examiner

*Primary Examiner*—Francis J. Jaworski
(74) *Attorney, Agent, or Firm*—Fitch, Even, Tabin & Flannery

(57) ABSTRACT

Ultrasonic devices for preventing microbubbles and/or microparticles from reaching the brain during a PCI, or cardiovascular surgery. Devices 27 and 77 are designed for implantation in the chest cavity and operate in combination with needle vents or other vent systems for removing diverted microbubbles. Systems 77 and 83 are designed for noninvasive employment. Devices 57 and 87 are particularly designed to prevent microbubbles from reaching the great origins of the carotid arteries and/or for diverting bubbles that might reach the vicinity and otherwise pass through. Improved devices 11 and 94 separate microbubbles from a flowing bloodstream and produce a cleansed stream.

27 Claims, 5 Drawing Sheets

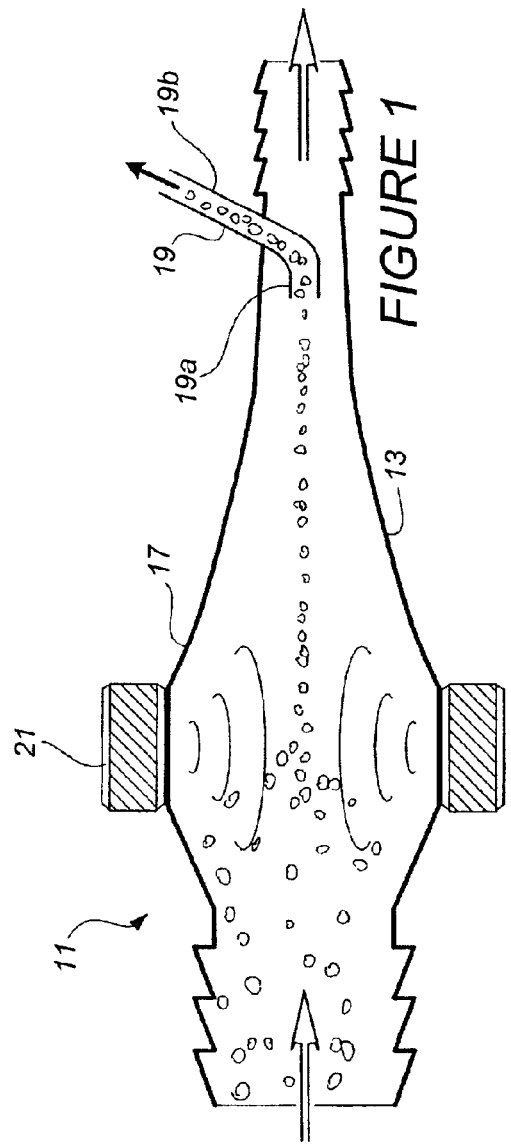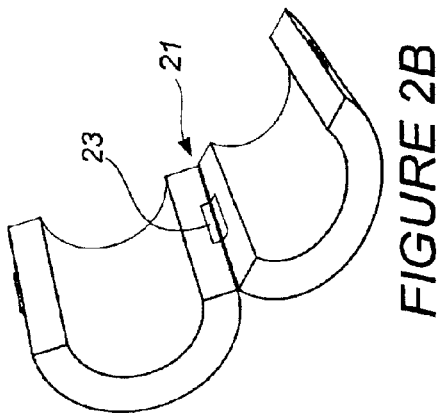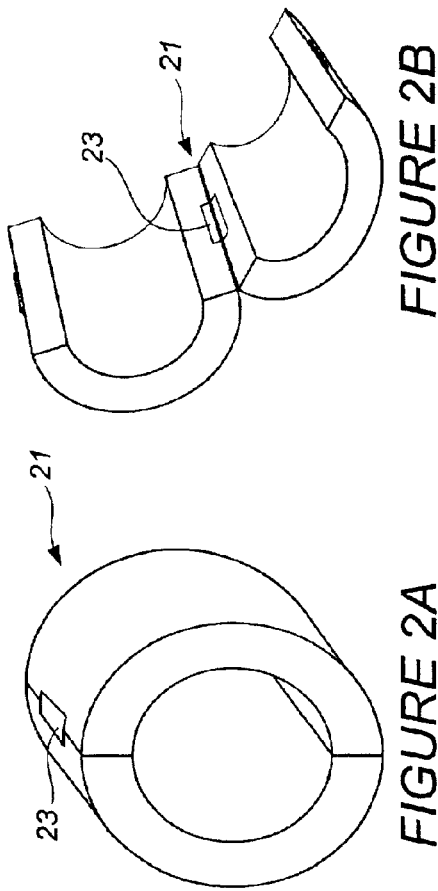

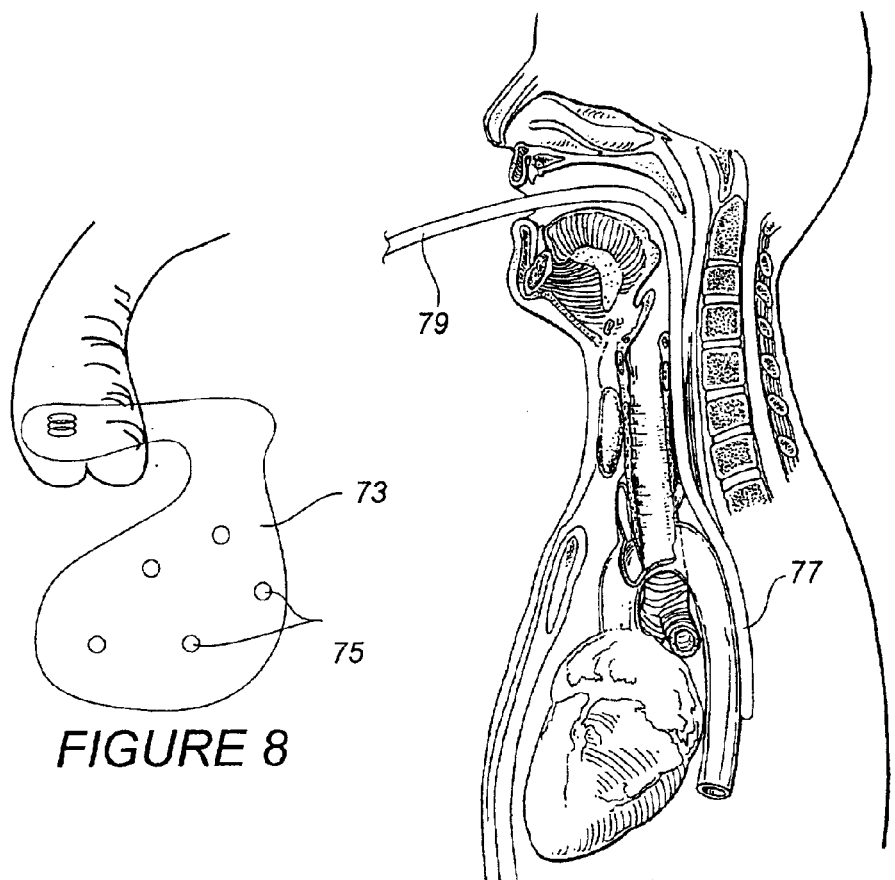
FIGURE 8
FIGURE 9
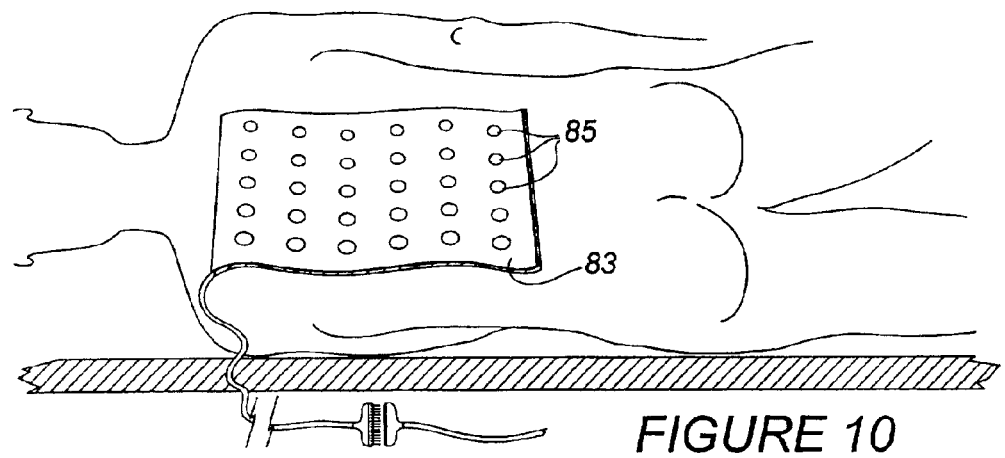
FIGURE 10

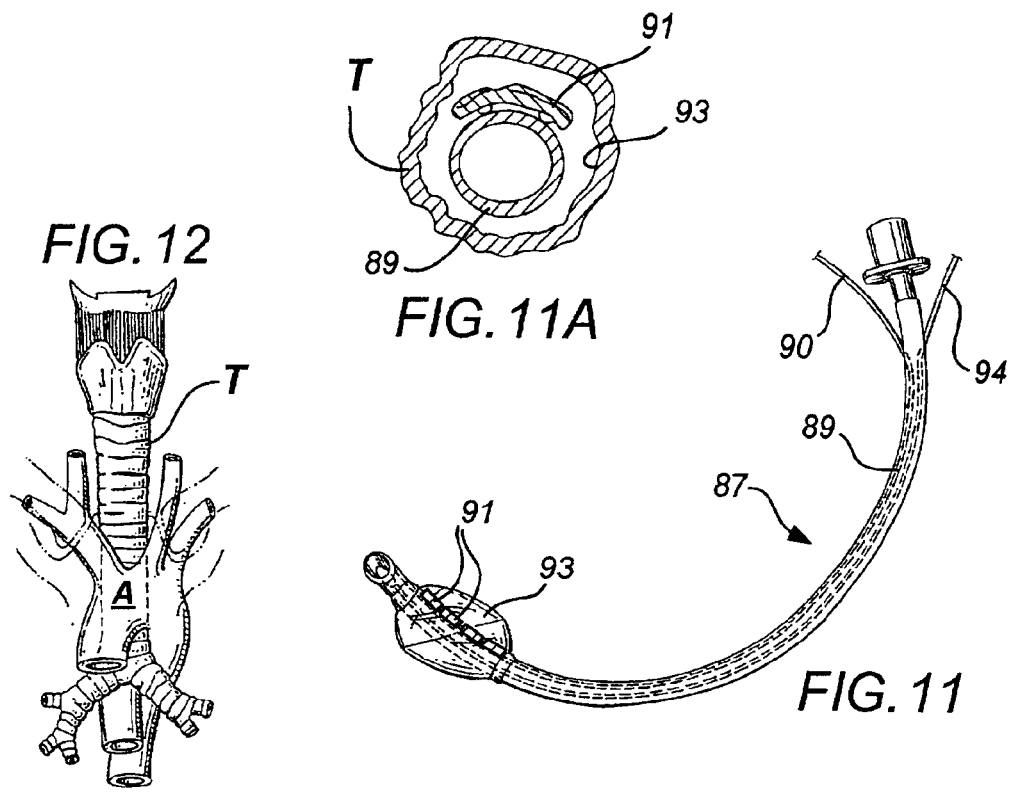
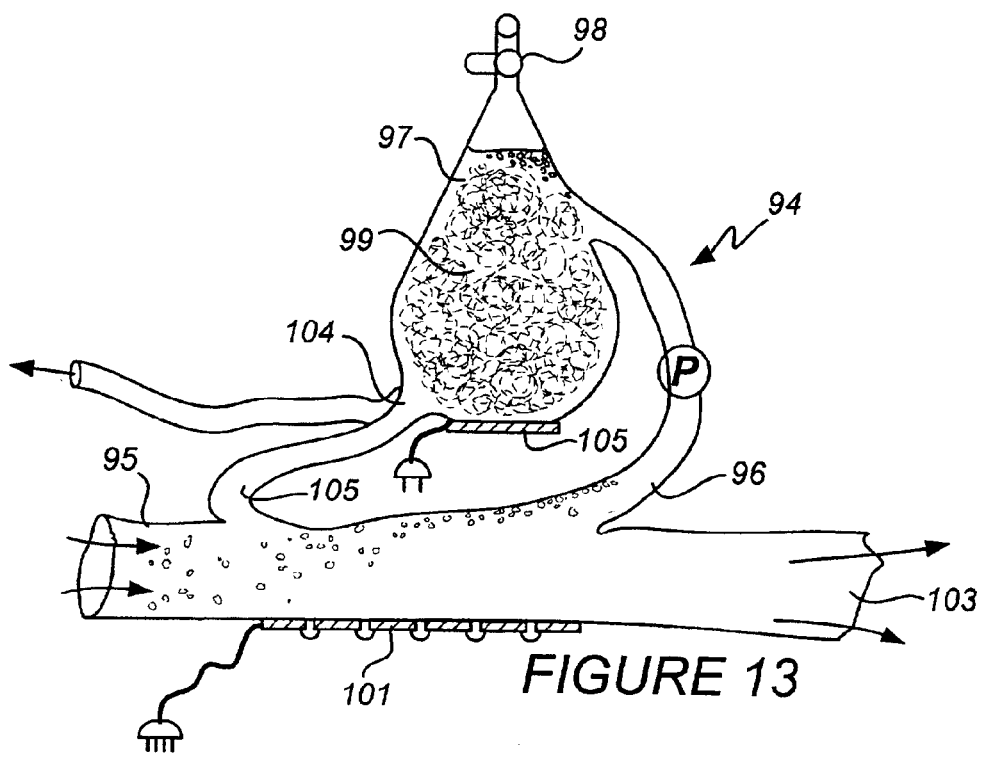

ULTRASONIC MEDICAL DEVICE

This application is a continuation of PCT/IB00/01785, filed Dec. 4, 2000, which application claimed priority from U.S. Provisional Application Ser. No. 60/190,839, filed Mar. 20, 2000, and U.S. Provisional Application Ser. No. 60/169,226, filed Dec. 6, 1999, the disclosures of which are expressly incorporated herein by reference.

FIELD OF THE INVENTION

The invention relates generally to devices which employ ultrasonic waves for removal of contaminants from liquids, and more particularly the invention provides devices and methods for medical treatment that employ the imposition of ultrasonic energy to a flowing stream of blood so as to deflect and/or remove small bubbles and/or particles that may be entrained therein.

BACKGROUND OF THE INVENTION

Sound waves may be viewed as being generally mechanical from the standpoint that they consist of the vibration of molecules about their equilibrium positions, and they are accordingly best transmitted through solid media. Sound waves with frequencies above the upper limit audible to the human ear (about 18,000 Hz) lie in the ultrasonic range. There are two main classes of ultrasound presently in clinical use: (1) High frequency (5–7 MHZ),low-power ultrasound, which is employed extensively in diagnostic ultrasonography; and (2) Low-frequency (20 to 45 kHz), high power ultrasound which has recently been put to therapeutic use.

It has been known for some time that the application of acoustic energy or force for a stream of flowing liquid, such as blood, will have an effect upon the behavior of gas bubbles entrained therein. An article entitled "Acoustic Effects on Gas Bubbles In the Flows of Viscous Fluids and Whole Blood" appeared in the *Journal of Acoustical Society of America*, 53, 5, 1327–1335, I. C. Maceto and Wen-Jeo Yang (1973), which discussed the use of acoustic or ultrasonic waves to trap small bubbles against the wall of the tube in which the liquid stream is flowing, using liquids that resemble whole blood in their rheological property; it was shown that the bubbles could be deflected and trapped against the sidewall of the tube in which flow is occurring. In 1992, Schwarz, Karl Q. et al., published an article entitled "The Acoustic Filter: An Ultrasonic Blood Filter for the Heart-Lung Machine", in the *Journal of Thoracic and Cardiovascular Surgery*, 104, 6, 1647–1653 (December 1992). This article indicated that microbubbles in a chamber can be pushed to the opposite end of the chamber where they can be accumulated and eventually carried through a waste port, as a result of which it would be feasible to use acoustic radiation force to filter small gas bubbles from blood, while cautioning that such ultrasonic energy might cause implosion of gas bubbles that could potentially result in blood trauma, e.g. hemolysis, and thus should possibly be avoided for such reason.

U.S. Pat. No. 5,022,899, entitled Sonic Debubbler for Liquids, discloses devices that employ an ultrasonic transducer to produce low power anisotropic sound waves at about the resonant frequencies of bubbles to drive the bubbles in a specific direction where they would be rejected by being drawn out through a fluid outlet port or trapped in a disposable open cell bubble trap. Power levels are regulated so as to remain below a level which would cause hemolysis from cavitation. U.S. Pat. No. 5,334,136 shows a system for reducing post-cardiopulmonary bypass encephalopathy due to microembolization of the brain of a patient as a result of microbubbles that may arise during open-heart surgery when a cardiopulmonary bypass machine is employed. The patient's bloodstream is subjected to an ultrasonic traveling wave which is directed across the stream of blood without reflection so as to sweep the blood clean of microbubbles without inducing blood cell trauma. The microbubbles are carried by the traveling wave to a waste exit port.

Although such early devices as those in the above-identified U.S. patents showed the principle to be sound, devices for more efficient operation have continued to be sought as well as devices that could be associated directly with the human body itself so as to have an effect upon the internal bloodstream in a patient who is undergoing treatment.

SUMMARY OF THE INVENTION

The invention provides devices for the removal of contaminants from liquids, and more particularly devices for medical treatment of a patient undergoing cardiac surgery or a percutaneous cardiological intervention (PCI), which devices utilize acoustic or ultrasonic energy to cause microbubbles and/or microparticles traveling in a flowing stream of liquid, such as blood, to be deflected in a specific manner in order to efficiently either effect their removal from the flowing stream or to block their entry to a critical portion of the human body, such as the neck vessels leading to the brain.

In one particular aspect, the invention provides a medical treatment device for removing microbubbles and/or microparticles from the blood of a patient, which device comprises transducer means for surrounding a conduit within which a stream of liquid is flowing, a sidestream-removal tube unit for location downstream of said transducer means and axially within said conduit which is operable to withdraw the central portion of said flowing stream, and power means for operating said transducer means to direct ultrasonic energy radially inward about 360° so as to concentrate microbubbles and/or microparticles centrally in the flowing stream where they can be withdrawn through said tube unit.

In another particular aspect, the invention provides a medical treatment device for removing microbubbles and/or microparticles from a patient's bloodstream, which device comprises transducer means for association with the exterior surface of the posterior side of the aorta in the general region of the transverse sinus, means for powering said transducer means to generate ultrasonic waves that are directed toward the anterior side of the aorta, a needle vent for insertion into the anterior side of the aorta downstream of the transverse sinus, and means for removing blood and microbubbles and/or microparticles through the needle vent.

In one more particular aspect, the invention provides an improved bubble trap which is designed to physically remove air bubbles and microparticles from a sidestream of liquid such as that diverted in the device of FIGS. 1 and 2, which would be particularly useful in treating diverted blood from a heart-lung machine or the like.

In a further particular aspect, the invention provides a medical treatment device for preventing microbubbles and/or microparticles from entering the neck vessels of a patient comprising collar means for association with the exterior of the neck of a patent undergoing surgery that contains multiple transducers in selected locations focused to direct ultrasonic waves downward and inward at both great origins of the neck vessels at the arch of the aorta, and means for powering such transducers so as to send ultrasonic waves that cause microbubbles and/or microparticles to deviate within the flowing bloodstream so as not to enter said great origins and instead travel to the lower part of the patient's body.

In yet another particular aspect, the invention provides a method for generating ultrasonic waves either adjacent an external surface of the body of a patient or within the esophagus or trachea of a patient and directing those waves toward the aorta so as to cause microbubbles and/or microparticles traveling in the patient's bloodstream in the aorta to deviate in a preselected direction from normal direction of flow.

In still another particular aspect, the invention provides a method for treating a patient undergoing a PCI, or open-heart surgery, so as to remove microbubbles and/or microparticles from the blood of the patient, which method comprises focusing ultrasonic waves into the left ventricle and/or the ascending aorta of the patient to direct microbubbles and/or microparticles so they will reach a region along the anterior wall of the ascending aorta, and withdrawing said microbubbles and/or microparticles from the bloodstream through vent means extending through the anterior wall of the aorta.

BRIEF DESCRIPTION OF THE DRAWINGS

FIG. 1 is a schematic view of a medical treatment device embodying various features of the invention shown as it might be operated with the stream of blood exiting from a heart-lung machine which would be hooked up to a patient undergoing cardiac surgery.

FIGS. 2A and 2B are perspective views of a transducer employed in FIG. 1 shown in the closed and open positions.

FIG. 8 is a schematic view of a pad embodying various features of the invention and containing multiple transducers that might be used in the chest of a patient positioned underneath the heart as a part of a method of medical treatment, e.g. during open heart surgery.

FIG. 9 is a view illustrating medical treatment wherein a modified esophageal probe is positioned in the esophagus so as to direct microbubbles and/or microparticles in the aorta anteriorly to a withdrawal vent, e.g. the smaller lumen of a double-lumen cannula such as that shown in FIG. 6.

FIG. 10 is a view similar to FIG. 8 showing an alternative embodiment of the transducer-carrying pad that might be exteriorly placed against the back of a patient.

FIG. 11 is a perspective view of an endotracheal tube useful in one method of the invention which is shown with a positioning balloon inflated.

FIG. 11A is a cross-sectional view enlarged in size, taken along the line A—A of FIG. 11 showing the tube positioned in a patient's trachea.

FIG. 12 is a front view of the ascending aorta, the trachea and the esophagus which shows the bifurcation of the trachea and the close relationship between the trachea and the aortic arch between the ascending aorta and the descending aorta.

FIG. 13 is a schematic view which shows an improved ultrasonic debubbler useful for treating a diverted stream of liquid containing air bubbles and/or microparticles and producing a cleansed stream with all such contaminants removed.

DETAILED DESCRIPTION OF THE PREFERRED EMBODIMENTS

Figure 3:
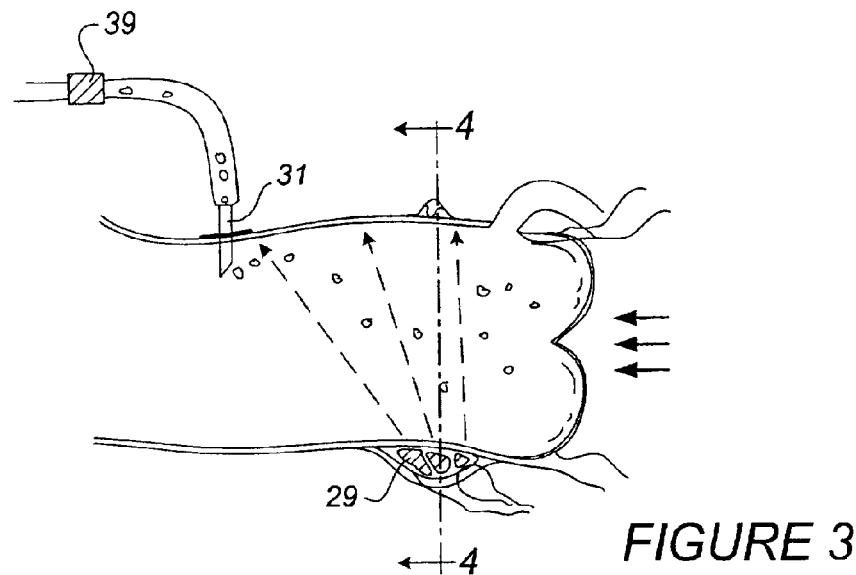
FIG. 3 is a sagittal, longitudinal sectional view showing the aortic root, a needle vent to which suction is applied, and an acoustic device which includes multiple piezoelectric crystals (shown in cross-section), with the plane along which the view is taken passing vertically through the transverse sinus.

Inasmuch as air bubbles found in the bloodstream will often originate in a heart-lung machine, manufacturers of such machines have provided very fine blood filters located between the heart-lung machine and the patient. Unfortunately, despite such precautions, there are substantial indications that so-called "arterial-line" microbubbles still reach the patient, and once they reach the patient, they very likely will reach the brain where they will frequently result in neurological damage. It has now been found that a more efficient bubble-removal device can be constructed which utilizes the known principles of the prior art devices.

Illustrated in FIG. 1 is an improved removal device for withdrawing air bubbles or microparticles that might be entrained in a flowing stream of liquid, such as blood which is being discharged from a heart-lung machine or some similar device. The removal device 11 includes a tubular body 13 which is formed with threaded connectors 15a and 15b respectively at the inlet and outlet ends. The body is circular in cross-section and has an enlarged region 17 near the inlet end, of greater diameter than either the inlet or the outlet, which gradually smoothly reduces to an outlet having about half of the enlarged diameter. A vent tube 19 is located just upstream of the outlet in a region where the tube 13 has narrowed to a continuous diameter section. The vent tube is fixed to the wall of the tubular body 13 and has an entrance section 19a that is coaxial therewith and an oblique side section 19b through which a small stream of liquid is removed from the main stream flowing through the device 11.

Surrounding the enlarged diameter region 17 is a transducer 21 of annular shape. As depicted in FIGS. 2A and 2B, the annular transducer 21 is preferably made in two halves that are interconnected by a hinge 23 so that the transducer might be placed around an existing conduit if desired. The space between the transducer 21 and the tubular body 13 is filled with water or with a jelly substance so that there will be a good flow path for acoustic energy therethrough.

When for example blood being discharged from a heart-lung machine is being returned to the body of the patient, it may include small bubbles of air and/or microparticles, which it is important be removed prior to return to the body of the patient. By discharging the stream into an enlarging region, there is more time for particles and/or bubbles to be acted upon by acoustic energy at this point. The annular transducer 21 is operated so as to generate ultrasonic waves and direct them radially inward towards the center for 360° about the circumference of the tube. Accordingly, microbubbles and/or microparticles will be uniformly concentrated in the very center of the flowing stream and will accordingly be removed through the downstream vent tube 19 through which there is continuous withdrawal of a sidestream using a roller or sinusoidal pump, or any other suitable type of pump that will direct the sidestream to a filter to remove microparticles and small bubbles, such as that described hereinafter with respect to FIG. 13. If the liquid being treated is blood, one would then recirculate the blood to the heart-lung machine or return it for another pass through the removal device.

Figure 4:
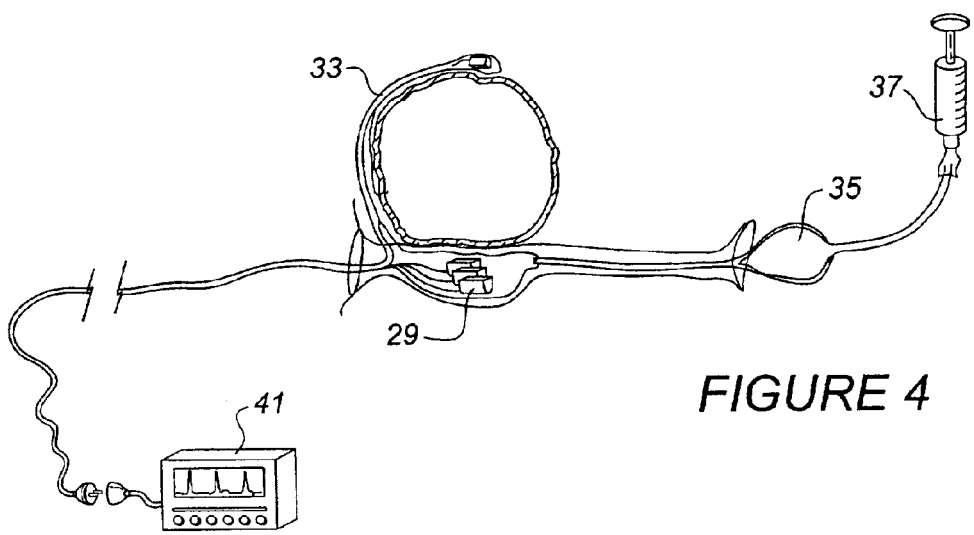
FIG. 4 is a view taken along line 4—4 of FIG. 3, showing the root of the aorta with the device situated in the transverse sinus, stabilized with a spring on the patient's right side of the aorta and with tension created by inflation of a rubber balloon located on the patient's left side.

Illustrated in FIGS. 3 and 4 is a removal system 27 which is designed for association with the ascending aorta at a location just downstream from the aortic valve. The device 27 is designed for placement in the transverse sinus and is operated so that air bubbles and/or microparticles during all levels of the flow of blood from the left ventricle of the heart are directed toward the anterior aspect of the ascending aorta. A transducer in the form of multiple piezo crystals 29 arranged as an annular array is located exterior of the aorta with the crystals being aimed in different directions generally across the blood flow. Flow rate is monitored and flow rate-dependent, sequential pulses are used to cause the air bubbles to translate in an anterior direction as well as to cause them to cavitate and coalesce with other small bubbles to create larger ones. A needle vent 31 is inserted through the anterior wall of the aorta, and suction is continuously applied during active operation.

Suitable signals to cause generation of high frequency and/or low frequency ultrasound waves may be transmitted simultaneously by activating a pulse generator connected to the various piezo crystals. The employment of a multitude of crystals is preferred so that some may be dedicated to providing high frequency sound waves; however, it may also be satisfactory to use the same crystals to alternately produce ultrasound of the two different desired frequencies. Low, high and mixed frequency sound waves are generated as long as the system continues to detect bubbles passing through the needle vent. Only when no further bubbles are being detected, as by a Doppler sensor, is the needle vent operation discontinued and the vent removed. The system can thereafter be switched into another mode so that it operates as a Doppler-type flow-measuring device. In this mode, the system is able to provide the surgeon with important information to allow a studied decision to be made as to when the patient may be taken off the bypass machine, e.g. by providing indexes such as Cardiac output in liters/min or in liters/min/Kg body weight.

As shown schematically in FIG. 4, which is a cross-section through the aorta looking downstream, the device may include a spring-like holder 33 that extends for about 210° of the circumference of the aorta and positions the piezo crystals 29 at the desired posterior location. Thus, the holder 33 will generally be associated with the patient's right side of the aorta, and tension in the spring-like device is created simply by the inflation of a rubber balloon 35 located on the patient's left side as at the location of the transverse sinus with the balloon being simply inflatable through a simple syringe 37 or other device for feeding air into the balloon. To monitor the bubbles that are being removed through the needle vent, a Doppler sensor 39, as well known in the art, may be employed which would feed information to a central control box 41. The control box 41 could be placed next to other monitoring devices used during cardiac surgery and controlled by an anesthesiologist. It would normally include the pulse generator for feeding energy to the piezo crystals 29 in an impulse-flow synchronizing system. If desired, a suitable mechanism may also be included to monitor cardiac output measurements to assist the surgeon in deciding when the patient should be removed from the cardiopulmonary machine. In addition to a read-out from the Doppler sensor 39, the control box might also have acoustic and visual signal displays. Suitable cables leading from the control box 41 would connect to the transducer piezo crystals 29 and to the Doppler sensor. As with all medical devices of this type, the portions that should be implanted within the body may be of disposal design or they could be made permanent by employing materials that can be sterilized after use.

Figure 5:
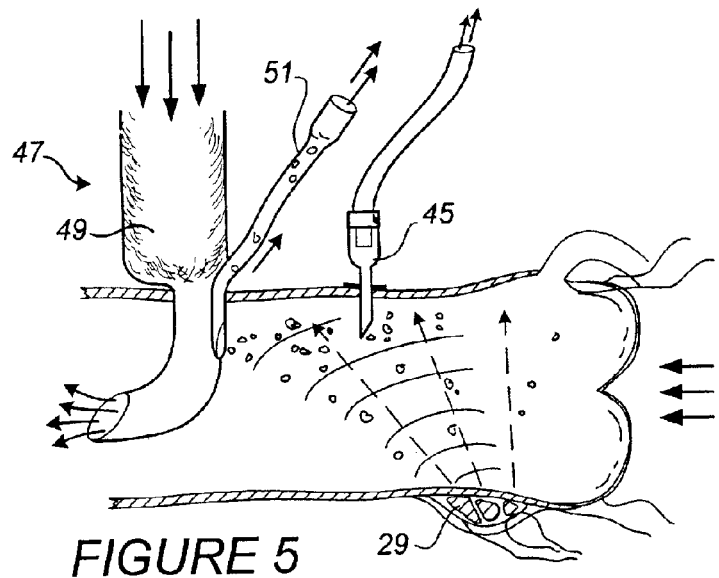
FIG. 5 is a view of an alternative medical treatment device generally similar to that shown in FIGS. 3 and 4 which employs a double lumen cannula.
Figure 6:
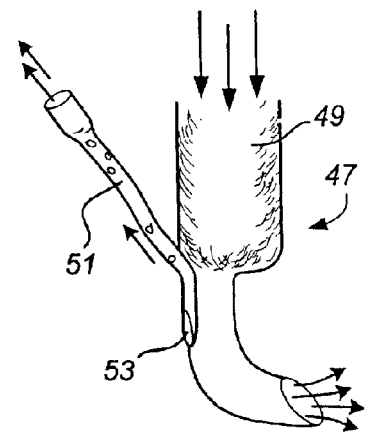
FIG. 6 is a perspective view showing an arterial-line double lumen cannula.

Shown in FIGS. 5 and 6 is an alternative device wherein a similar transducer system to that depicted in FIGS. 3 and 4 is employed. An array of piezoelectric crystals 29 is located along the posterior surface of the aorta just downstream of the aortic valve, and although a needle vent 45 is shown, it is optional because, just downstream thereof in the anterior wall of the aorta, there is inserted a double-lumen arterial-line cannula 47.

When a patient is connected to a heart-lung machine, the venous blood is drained from the right atrium and transmitted to the heart-lung machine for oxygenation before being returned to the patient's arterial system. A return connection is generally established through the installation of an aortic cannula which penetrates the aorta via a stab-wound insertion into the anterior aspect of the ascending aorta. A needle vent 45 similar to that depicted in FIG. 5 may be employed at about this same general location just upstream of the aortic cannula to remove air bubbles in the oxygenated bloodstream flowing downstream from the aortic valve that would otherwise enter the arterial system of the patient. The operation of such a needle vent 45 is of course greatly enhanced by the ultrasonic wave-generating device, as described with respect to FIGS. 3 and 4.

Using the double-lumen cannula 41 illustrated in FIGS. 5 and 6, a single penetration of the aorta can be used both to return the oxygenated blood to the circulatory system and to take the place of the needle vent shown in FIG. 3. However, it can also be used in combination with a needle vent, as illustrated in FIG. 5, to supplement operation during the major portion of the cardiac surgery. Sometimes not all of the blood will be drained from the right atrium into the heart-lung machine, and such will be oxygenated in the lungs if the patient is being ventilated. As a result, this blood will reach the left atrium and thereafter will flow through the left ventricle. Moreover, during the performance of the proximal anasthomoses in coronary artery bypass surgery, for example, constant suction is applied to the needle vent, thus causing some air to enter into the coronary arteries, the aorta and the left ventricle because the aorta is under negative pressure.

The returning blood flows through a large diameter cannula 49 of the device into the ascending aorta, while a second smaller diameter cannula or tube 51, which is integrally attached to the exterior of the large diameter cannula, is used to carry out a function similar to that of the needle vent 33 in FIG. 3. The small cannula 51, which alternatively could be located interior of the large cannula with an appropriate opening in the sidewall, has an opening 53 that faces in exactly the opposite direction from that of the lumen of the large cannula from which the oxygenated blood is being discharged. Accordingly, the return stream of oxygenated blood is discharged so as to flow downstream through the ascending aorta, whereas the smaller diameter lumen is strategically located so as to remove a small stream of potentially bubble-containing blood that has passed through the aortic valve, i.e. in order to prevent potential bubbles in the blood from reaching the brain and other susceptible organs. The preferable inclusion of transducers 29 exterior of the aorta, as optionally depicted in FIG. 5, directs any bubbles toward the needle vent and/or the small diameter lumen as explained hereinbefore. Such a small side stream of blood being removed through the smaller lumen 51, and optionally also through a needle vent 45, is achieved through the use of a suction pump or the like, as explained with respect to the FIG. 3 embodiment, and all this blood is returned to the reservoir of the heart-lung machine during this portion of the operation.

When used with the exclusion of any needle vent, the double-lumen cannular 47 avoids the necessity of having to make a second puncture in the aorta; however, even when used in combination with a needle vent 45, the device allows venting to continue after the time that a needle vent 45 is usually removed to allow the construction of the proximal anasthomoses on a beating heart, as is commonly done in coronary artery by-pass surgery. In by-pass surgery, it is common to connect the vein grafts to the ascending aorta at about the location where the needle vent 45 is located in FIG. 5. Accordingly, when the connections to the aorta are ready to be made, the needle vent must be removed, and at this time, the heart will begin beating so there will be some blood flowing out of the left ventricle through the aorta. Moreover, this period of time may be as long as about 45 minutes, i.e. from the time that the needle vent would be removed until the patient is taken off of the heart-lung machine. It can thus be realized that the ability to continue to remove a small stream of potentially bubble-containing blood through the novel double-lumen cannula can be particularly advantageous to the patient.

Figure 7:
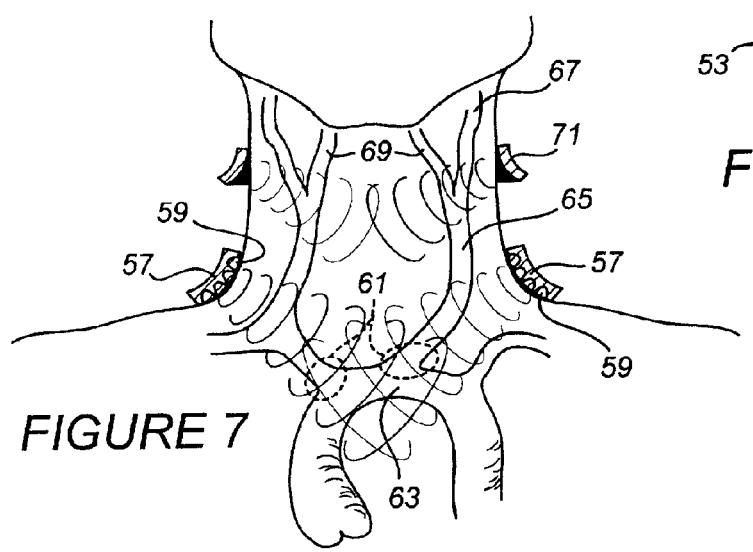
FIG. 7 is a view showing another embodiment of a medical treatment device embodying various features of the invention which is designed to be associated about the neck of a patient undergoing cardiac surgery or a PCI.

Depicted in FIG. 7 is a collar 57 that is sized to be placed around the neck of a patient who is undergoing a PCI, such as an angioplasty or an angiography, by-pass surgery, valve repair or replacement or other cardiac surgery. The collar 57 may encircle the patient's neck for 360°, or it may be a U-shaped piece of flexible material having a pair of arms that carry the transducers. At selected sites in the interior surface of the collar 57, single or multiple transducers 59, e.g. piezoelectric elements, are embedded. These may be placed on only one side of the neck, but they are preferably placed on both sides as shown in the FIG. 7 embodiment. The transducers 59 are connected by electric cables to a pulse generator in a control box (not shown) such as that in FIG. 4. The transducers 59 are oriented so as to be aimed at both great origins 61 of the neck vessels, where the carotic arteries leave the aorta 62 along the arch 63 of the aorta and travel upward to the brain. When a patient is placed on the heart-lung machine, ultrasonic waves are generated by the transducers 59 and sent toward the two origins 61, thereby effectively blocking both large and/or small air bubbles and microparticles, such as atherosclerotic-detached debris particles from the patient's aortic wall as well as thrombi and calcium-cholesterol particles, from entering into the neck vessels. These directional waves cause any bubbles to deviate from a potential path that would otherwise carry them through a great origin 61; instead, they remain in the blood flow in the aorta, which is flowing into the remainder of the body, e.g. to the liver, the gut, the legs, etc. As a result, potential damage to the brain which is particularly sensitive to air in the bloodstream is avoided.

Because the collar device may need to be operated for a lengthy period of time during a PCI or open-heart surgery, the collar 57 preferably contains a set of transducers 59 on both sides of the neck, as shown, and the set of transducers on each side is focused upon both of the great origins 61. In order to avoid potential adverse side effects upon the body itself from these ultrasonic waves, the device is operated to alternately send signals first to the set on one side for a few minutes and then to the set on the other side to generate the desired wave patterns in the regions of the great origins 61 without substantially heating or otherwise affecting the patient's flesh.

Because no system of this type is perfect, it may also be desirable to include a second or auxiliary smart collar 71 that is focused at locations downstream of the great origins 61, namely the location where the carotid arteries split prior to entering the skull. At this location there are two branches, an internal carotid 67 which supplies the brain and an external carotid 69 which supplies the facial structure. This auxiliary collar 71 will contain transducers that are focused at the region just upstream of the junction where the split into the internal and external carotids occurs, and it will serve as a back-up that will cause any bubbles and/or solids, i.e. atherosclerotic or other debris particles, that may enter to the great origin to be diverted to the external carotid which supplies the facial structures. Thus, it provides a second level of defense to guard against such reaching the brain.

Shown in FIG. 8 is an ultrasonic device which focuses on the heart itself and particularly on the left ventricle. The device includes a relatively flat pad 73 of a size and shape to generally be inserted below the heart in a supine patient and through the transverse sinus so that the heart would rest upon the pad, with the pad being positioned below the region of the left ventricle. The pad 73 has incorporated therein a plurality of transducers 75 which are operated so as to create ultrasonic waves that move vertically upward through the blood in the left ventricle and thus preferentially cause microbubbles to collect at the highest vertical point or apex in the left ventricle of the patient, who is positioned in the supine position with his chest open. The device could be operated separately, or it could be operated in combination with a device such as that shown in FIGS. 3 and 4 which focuses upon microbubbles in the bloodstream that have traveled through the aortic valve. Once the patient has been taken off the heart-lung machine, and optionally at various times during the operation, the surgeon may remove collected air from the heart by simple insertion of a needle into the left ventricle at its apex, withdrawing the air and a minor amount of blood by suction.

As an alternative to placing such a transducer-carrying pad beneath the heart, one can utilize the proximity of the esophagus to the left ventricle of the heart to create a similar effect from the interior of the esophagus. A commercially available trans-esophageal probe can be easily modified so as to carry a set of transducers similar to those shown in the collar 57 in FIG. 7. These transducers can be aligned so as to generate and direct ultrasonic waves to accomplish a pattern of upwardly traveling ultrasonic waves roughly similar to those created by the pad shown in FIG. 8.

Illustrated in FIG. 9 is the use of a modified esophageal probe 77 which contains transducers suitable for directionally transmitting ultrasonic waves in a manner similar to the transducers 29 described previously. The esophagus is located in the body adjacent the left ventricle of the heart and the aorta. Esophageal probes that include ultrasonic transmitters and receivers are well known in the art and are described in U.S. Patents such as U.S. Pat. Nos. 5,409,010, 5,105,819, 4,757,821 and 3,951,136. Such probes of this basic nature are commercially available today throughout the world by vendors such as Deltex Medical, Medtronic Functional Diagnostics and Neomedix Systems and other vendors. Although probes of this general type have heretofore been used for diagnostic purposes, it has now been found that by employing transducers of the type herein described suitable for creating ultrasonic acoustic energy in the ranges of interest, a modified esophageal probe can be created incorporating such transducers and no receivers, such as are included in esophageal probes presently in use. Multiple transducer assemblies for creating ultrasonic waves for other purposes are shown in U.S. Pat. Nos. 6,126,619, 5,879,314 and 5,269,291. Signals would be sent to the transducers through an appropriate electrical connection 79 outside of the body so as to travel along the probe to the location of the set of piezo crystals or the like and activate the transducers. By properly manipulating the esophageal probe, the surgeon will be able to align it to focus the ultrasonic waves so as to cause the microbubbles to be directed upward to the highest point in the left ventricle where they would collect and also focus waves to move anteriorly in the ascending aorta. Then, as previously described, either periodically, or at the end of the operation, the surgeon might manually lift the apex of the heart and puncture it with a suitable needle to withdraw the collected air by suction. Moreover, by also focusing ultrasound waves at the ascending aorta just downstream of the aortic valve, the device will also function in a manner similar to that described with respect to the transducers 29 in FIGS. 3 and 4 to cause gas bubbles and/or microparticles, such as atherosclerotic and other debris particles, to be diverted anteriorly to a location where a needle vent and/or a double lumen cannula would be installed in the aorta.

As an alternative to employing an esophageal probe for this function of diverting the gas bubbles in the heart or in the aorta as described above, it has also been found that such diversion can also be noninvasively achieved through the employment of a flat pad 83 that is positioned against the back of the patient undergoing surgery.

A large pad 83 having a plurality of transducers 85 is illustrated in FIG. 10 which is designed to be positioned entirely exteriorly adjacent the back of the patient. As shown, the pad would be adhered to the patient's back just posterior of the heart and the aorta in a similar manner to that in which ECG electrodes are attached. The surgeon handling the operation would decide which of the individual transducers 85 in the lattice-like array would be selectively activated so as to, for example, focus ultrasonic waves on the left atrium, the left ventricle and the ascending aorta. Thereafter, the selected transducers in the pad would be caused to operate, after the chest had been opened, to direct ultrasonic impulses for the same purpose as described hereinbefore with regard to the esophageal probe and with respect to the internal pad that was placed directly beneath the heart.

Instead of using a modified esophageal probe, a modified endotracheal tube 87 (illustrated in FIG. 11) may alternatively be employed in another noninvasive method of diverting microbubbles and/or microparticles from entering the great origins. As illustrated in FIG. 12, the ascending aorta is located adjacent the trachea (T), and the aorta arch (A) lies just above the bifurcation of the trachea. Accordingly, it can be seen that the location of a transducer at this location in the trachea will allow ultrasound to be directed at the aortic arch, and it can be employed in the same manner as the collar 57 for diversion of contaminants away from the great origins.

Endotracheal tubes have been used for some time to carry ultrasonic transducers and receivers in order to monitor the rate of flow of blood in the aorta, and U.S. Pat. Nos. 4,886,059 and 4,722,347 disclose such devices for use in monitoring blood flow.

The modified endotracheal tube 87 consists of flexible plastic tubing 89 of a length sufficient to extend from outside the body to the vicinity of the bifurcation of the trachea, entering either through the nasal or oral cavity or through a surgical opening in the case of a patient who had a tracheotomy. The illustrated device is adapted for oral insertion. Near the distal end, a transducer comprising a plurality of piezoelectric elements 91 is mounted on the exterior surface of the tubing 89. Electrical conductors 90 extend the length of tubing 89 for connection of a pulse generator (not shown) to the transducers.

To positively locate the tube 87 in the trachea, T, and to provide a good path between the transducers 91 and the inner wall of the trachea, a donut-shaped cuff or balloon 93 is provided which also seals the trachea. The endotracheal tube 87 is placed to locate transducers 91 in the trachea, generally at a location just above the tracheal bifurcation, and then rotated as needed to point them toward the aortic arch. For ventilation purposes it is necessary to seal the trachea, and the transducers 91 should be held in position within the trachea and focused toward the aortic arch. The donut-shaped cuff or balloon 93 effectively seals the trachea and holds the tube and the transducers that it carries in place. Inflation of the balloon 93 is accomplished via an inflation tube 94 using conventional fluid, preferably acoustic jelly or water, that assures good acoustic transmission to the tracheal wall. In other respects, the endotracheal tube 87 is constructed in accordance with recognized ANSI standards for construction of endotracheal tubes. In particular, the distal end suitably is provided with a standard bevel opening and oppositely directed Murphy eye.

Multiple transducers 91 may be designed to occupy an elongated annular array, as best seen in FIG. 11A, where they would cover an arc of about 90 to 120° of the exterior of the plastic tubing 89 at a location near the distal end thereof within the inflatable cup, and the device would be oriented by the anesthesiologist so that they would face the aortic arch. Because of the proximity between the trachea and the arch of the aorta, it can be seen that this device can be actuated and manipulated from outside the body of the patient to noninvasively effectively divert potentially harmful microbubbles and/or microparticles so they do not enter the great origins.

In various of the aforedescribed devices, a separate sidestream of blood carrying the microbubbles and/or microparticles is diverted from a main bloodstream. Although various methods have long been provided for filtering this stream to remove these contaminants, an improved and particularly effective ultrasonic bubble trap 94 is illustrated in FIG. 13 which can be used for removing bubbles and microparticles from a flowing stream of liquid. The improved trap includes a main tube 95 which has a side outlet 96 that leads to a valved flask 97 or the like, entering at a location in the upper vertical half thereof. A pump P, such as a roller or sinusoidal pump, is included in the line 96 and can be used to raise the liquid to a higher vertical level above the tube 95. A normally closed valve 98 is provided at the apex of the flask, and the body of the flask is filled with a fibrous material 99 that is inert to blood or whatever liquid is being treated. Located below and upstream of the entrance to the side outlet is an elongated array of transducers 101 operated as hereinbefore described so as to generate ultrasonic waves that deflect microbubbles and/or microparticles upward against the upper wall of the tube 95 where they will be carried out the side outlet 96 with a small stream of liquid while the remainder of the liquid flow, now cleansed of these contaminants, flows downstream to the outlet 103 from which it might be sent to a reservoir, or if the liquid is blood, it would be ultimately returned to the patient. Once the liquid enters the flask 97, any microparticles would tend to adhere to the fibrous debubbling material 99 while air, via gravity, travels upward and collects in the upper region of the flask from which it can be periodically withdrawn through the valve 98. The flask may be mounted on any horizontal surface so that the liquid flows downward through the fibrous material 99 and out a lower outlet 104 driven by gravity. The flask 97 is optionally supported upon a pad 105 which contains additional transducers that are focused upward and actuated by a pulse generator (not shown). If the liquid being treated is blood, the establishment of upwardly directed ultrasonic waves will assure the separation of all microbubbles therefrom rather than relying upon gravity alone. In the illustrated version, the cleansed sidestream is returned to a side inlet 106 located upstream of the side outlet 96 in the tube 95. Alternatively, the cleansed stream could be instead directed via an outlet tube (indicated by dot-dash outline) to a Cardiotomy reservoir.

Although the invention has been described with regard to a number of preferred embodiments, it should be understood that various changes and modifications as would be obvious to one having ordinary skill in this art may be made to the invention without departing from the scope thereof which is defined in the appended claims.

What is claimed is:

1. A medical treatment device for preventing microbubbles and/or microparticles from entering the neck vessels of a patient comprising
    collar means for association with the exterior of the neck of a patient undergoing treatment which might give rise to the creation of microbubbles and/or microparticles in the bloodstream, which collar means contains multiple transducers in selected locations such that they will focus ultrasonic waves that are generated in a collar region of the patient at the exterior of the neck and direct them downward and inward at both great origins of the neck vessels at the arch of the aorta, and
    means for powering such transducers so as to send ultrasonic waves that cause microbubbles and/or microparticles to deviate within the flowing bloodstream so as not to enter said great origins and instead travel to the lower part of the patient's body.

2. The medical treatment device according to claim 1 wherein there is provided an auxiliary pad means for association with the right and left sides of the neck of the patient generally adjacent said collar means and just upstream of the location where the carotid artery splits into the external and internal carotids.

3. A method for treating a patient undergoing cardiac surgery or a percutaneous cardiological intervention so as to prevent microbubbles and/or microparticles in the blood of the patient from entering the neck vessels of the patient which method comprises the steps of:
    directing ultrasonic waves into the ascending aorta of the patient, and
    focusing such waves to direct microbubbles and/or micropartircles toward a wail of the ascending aorta.

4. The method according to claim 3 wherein said ultrasonic waves are generated in a collar region of the patient at the extension of the neck and directed downward and inward at both great origins of the neck vessels at the arch of the aorta so as to cause microbubbles and/or microparticles to deviate within the flowing bloodstream so as not to enter said great origins and instead travel to the lower part of the patient's body.

5. A method according to claim 3 wherein:
    said ultrasonic waves are focused into the ascending aorta of the patient to direct microbubbles and/or microparticles so they will reach a region along the anterior wall of the ascending aorta, and
    said microbubbles and/or microparticles are withdrawn from the bloodstream through vent means which is extended through the anterior wall of the aorta.

6. The method according to claim 5 wherein said ultrasonic waves are generated from transducers carried by an esophageal probe inserted into the patient's esophagus and positioned at a location adjacent the ascending aorta and the left ventricle of the heart.

7. The method according to claim 5 wherein said ultrasonic waves are generated from transducers carried by an endotracheal tube inserted into the patient's trachea and positioned at a location adjacent the aortic arch.

8. The method of treatment according to claim 5 wherein said ultrasonic waves are generated by transducers carried in a flexible pad which is positioned below the heart of the patient so that the heart rests thereupon during surgery.

9. The method of treatment according to claim 5 wherein said ultrasonic waves are generated by transducers carried by a pad which is adhered to the back of the patient in the region of the left ventricle and the ascending aorta.

10. The method of treatment according to claim 5 wherein said ultrasonic waves are generated by transducers located within the chest cavity of the patient at a location just downstream of the aortic valve.

11. A medical treatment device for removing microbubbles and/or microparticles from a patient's bloodstream, which device comprises
    transducer means for association with the exterior surface of the posterior side of the aorta in the general region of the transverse sinus,
    means for powering said transducer means to generate ultrasonic waves that are directed toward the anterior side of the aorta,
    sidestream-removal means for insertion into the anterior side of the aorta downstream of the transverse sinus, and
    means for removing blood and microbubbles and/or microparticles through said sidestream-removal means.

12. The medical treatment device according to claim 11 wherein means is provided f or holding said transducer means in physical contact with the exterior surface of the aorta.

13. The medical treatment device according to claim 12 wherein said holder means includes a spring-like support that fits more than 180° about the aorta.

14. The medical treatment device according to claim 13 wherein expandable balloon means is located between said support and said transducer means to hold said transducer means firmly against the exterior surface of the aorta.

15. The medical treatment device according to claim 11 wherein said sidestream-removal means is formed integrally with an arterial-line cannula for returning blood from a heart-lung machine to the aorta downstream of the aortic valve so as to constitute a double-lumen cannula.

16. The medical treatment device according to claim 15 wherein said double-lumen cannula has a main passageway through which incoming blood exits downstream and a smaller lumen passageway having an opening which faces directly upstream.

17. A method for controlling flow in a blood vessel in a body of a patient, the method comprising:
- positioning one or more ultrasonic transducers to be appropriately located and associated with the body of a patient; and
- actuating at least one such transducer to transmit ultrasonic waves toward the blood vessel, which branches into at least a first branch vessel, so as to cause at least one of microbubbles and microparticles that may be flowing in blood in the blood vessel to be deflected away from the first branch vessel.

18. The method according to claim 17, wherein said positioning the one or more ultrasonic transducers comprises placing at least one transducer adjacent to the patient's neck.

19. The method according to claim 18, wherein the blood vessel is a common carotid artery, and wherein said positioning the one or more ultrasonic transducers comprises aiming at least one transducer toward a location in the body upstream of where the common carotid artery splits into internal and external carotid arteries so as to cause the at least one of the microbubbles and microparticles to be deflected away from the internal carotid artery.

20. The method according to claim 18, wherein positioning the one or more ultrasonic transducers comprises aiming at least one transducer toward an aortic arch of the patient at a location of a great origin of a neck vessel so as to cause the at least one of the microbubbles and microparticles to be deflected away from the branch vessel which is a neck vessel.

21. The method according to claim 17, wherein said positioning the one or more ultrasonic transducers comprises positioning at least one transducer within a chest cavity of the patient adjacent to the ascending aorta, and aiming the at least one transducer into the ascending aorta so as to cause the at least one of the microbubbles and microparticles to be deflected away front a great origin of a neck vessel.

22. The method according to claim 17, wherein said actuating comprises actuating at least one transducer according to a wave pattern selected so as not to substantially heat flesh of the patient.

23. A device for controlling flow in a blood vessel in a body of a patient which branches into at least a first branch vessel, said device comprising:
- a collar which is adapted to be placed around the patient's neck; and
- one or more ultrasonic transducers, fixed to the collar so as to be positioned in a selected location relative to the body when the collar is placed around the neck, and adapted, while so positioned, to transmit ultrasonic waves toward the blood vessel, so as to cause at least one of microbubbles and microparticles that may be flowing in blood in the blood vessel to be deflected away from the first branch vessel.

24. The device according to claim 23, wherein the blood vessel is a common carotid artery, and wherein at least one said transducer is adapted, when the collar is placed around the neck, to transmit the ultrasonic waves toward a location in the body upstream of where the common carotid artery splits into internal and external carotid arteries so as to cause the at least one of the microbubbles and microparticles to be deflected away from the internal carotid artery.

25. The device according to claim 23, wherein the blood vessel is an aortic arch of the patient and wherein at least one said transducer is adapted, when the collar is placed around the neck, to transmit the ultrasonic waves toward the aortic arch at a location of a great origin of a neck vessel so as to cause the at least one of the microbubbles and microparticles to be deflected away from the neck vessel.

26. The device according to claim 23, which includes a controller that is adapted to actuate at least one of the one or more transducers according to a wave pattern selected so as not to substantially heat flesh of the patient.

27. A device for controlling flow in an aorta in a chest cavity of a patient which device comprises:
- a holder, which is adapted to be placed in the chest cavity in association with the aorta; and
- one or more ultrasonic transducers, which are adapted to be fixed by the holder in proximity to the aorta and to transmit ultrasonic waves into the aorta which waves have sufficient power so as to cause at least one of microbubbles and microparticles flowing in the aorta which are so affected by said ultrasonic waves to be deflected away from a great origin of a neck vessel.

* * * * *